US007232925B2

(12) United States Patent
Mori et al.

(10) Patent No.: US 7,232,925 B2
(45) Date of Patent: Jun. 19, 2007

(54) PROCESS FOR PRODUCING (4E)-5-CHLORO-2-ISOPROPYL-4-PENTENOATE AND OPTICALLY ACTIVE FORM THEREOF

(75) Inventors: Nobuaki Mori, Ichihara (JP); Yasushi Matsumura, Ichihara (JP); Yoshitomi Morizawa, Yokohama (JP); Toshihiko Kaminuma, Yokohama (JP); Yuuichi Aoki, Yokohama (JP)

(73) Assignee: Asahi Glass Company, Limited, Tokyo (JP)

(*) Notice: Subject to any disclaimer, the term of this patent is extended or adjusted under 35 U.S.C. 154(b) by 227 days.

(21) Appl. No.: 11/147,255

(22) Filed: Jun. 8, 2005

(65) Prior Publication Data

US 2005/0228193 A1    Oct. 13, 2005

Related U.S. Application Data

(63) Continuation of application No. PCT/JP03/15694, filed on Dec. 9, 2003.

(30) Foreign Application Priority Data

Dec. 9, 2002 (JP) ............................. 2002-356651
May 21, 2003 (JP) ............................. 2003-143256

(51) Int. Cl.
*C07C 69/62* (2006.01)
(52) U.S. Cl. .................................................. 560/219
(58) Field of Classification Search ................ 560/219
See application file for complete search history.

(56) References Cited

U.S. PATENT DOCUMENTS

| 4,338,326 A | | 7/1982 | Cain et al. | |
| 4,492,799 A | | 1/1985 | Wheeler | |
| 4,532,236 A | | 7/1985 | Nickolson et al. | |
| 6,777,574 B1 | * | 8/2004 | Herold et al. | ................ 560/129 |
| 7,153,675 B2 | * | 12/2006 | Herold et al. | ................ 435/135 |

FOREIGN PATENT DOCUMENTS

| DE | 37 37 377 A1 | 5/1989 |
| WO | WO 01/9079 | 2/2001 |
| WO | WO 02/8172 | 1/2002 |
| WO | WO 02/092828 A2 | 11/2002 |

OTHER PUBLICATIONS

Robert A. W. Johnstone, et al., "A Simple Method for C-Alkylation", Journal of Chemical Research, XP-008053832, 1980, p. 283.
R. Garth Pews, et al., "1,1,1,-Trichloro-3-[5-(2,4,6,-Trifluoropyrimidyl)]-3,4-Epoxybutane", Journal of Fluorine Chemistry, vol. 42, No. 2, XP-002348693, 1989, pp. 179-186.
Takeo Harada, et al., "Synthetic Approach to Identification of Periplaneta Sex Pheromones", Tetrahedron Letters, vol. 33, No. 3, XP-002348694, 1992, pp. 369-372.
Arutyunyan et al, Armyanskii Khimicheskii Zhurnal, 1988, vol. 41, No. 8, pp. 522-524.
"Akad. Nauk Armyan, S.S.R. Khim. Nauki," 1960, vol. 13, (4), pp. 259-262 (Russia) (with English abstract).

* cited by examiner

*Primary Examiner*—Kamal A. Saeed
(74) *Attorney, Agent, or Firm*—Oblon, Spivak, McClelland, Maier & Neustadt, P.C.

(57) ABSTRACT

The present invention provides processes for producing a (4E)-5-chloro-2-isopropyl-4-pentenoate and an optical isomer of the (4E)-5-chloro-2-isopropyl-4-pentenoate, namely a process for producing a (4E)-5-chloro-2-isopropyl-4-pentenoate represented by the following formula (4), which comprises reacting a compound represented by the following formula (2) in the presence of an aprotic solvent (II) with a base (II) and then with (1E)-1,3-dichloro-1-propene to give a compound represented by the following formula (3), and dealkoxycarbonylating either ester in the compound represented by the following formula (3), and a process for producing a (S)-(4E)-5-chloro-2-isopropyl-4-pentenoate represented by the following formula (5), which comprises optically resolving a (4E)-5-chloro-2-isopropyl-4-pentenoate represented by the formula (4) obtained by the above-mentioned process (wherein R is a lower alkyl group or an aralkyl group).

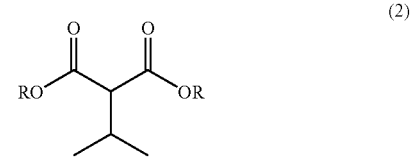

(2)

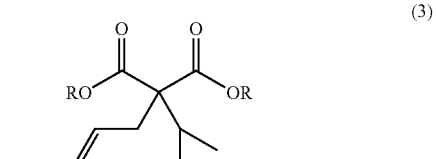

(3)

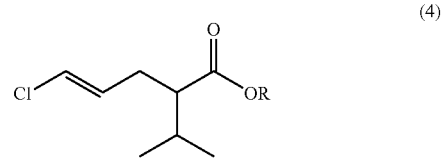

(4)

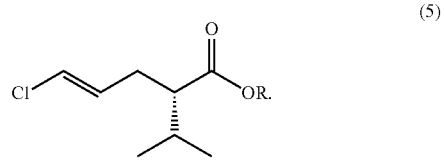

(5)

12 Claims, No Drawings

PROCESS FOR PRODUCING (4E)-5-CHLORO-2-ISOPROPYL-4-PENTENOATE AND OPTICALLY ACTIVE FORM THEREOF

This application is a Continuation of PCT/JP03/15694 filed 9 December, which claims priority under 35 U.S.C. 119 U.S. to JAPAN 2002-356651 filed 9 Dec. 2002 and JAPAN 2003-143256 filed 21 May 2003.

TECHNICAL FIELD

The present invention relates to a process for producing a (4E)-5-chloro-2-isopropyl-4-pentenoate useful as an intermediate for an agrochemical or a medicine. The present invention also relates to a process for producing an (S)-(4E)-5-chloro-2-isopropyl-4-pentenoate especially useful as an intermediate for an agrochemical or a medicine.

BACKGROUND ART

For synthesis of (4E)-5-chloro-2-isopropyl-4-pentenoates and their analogues, the following processes have been reported.

(1) A process for producing a 5-chloro-2-isopropyl-4-pentenoate by reacting methyl isopentanoate with 1,3-dichloro-1-propene in the presence of lithium diisopropylamide (LDA) at an extremely low temperature (−78° C.) (U.S. Pat. No. 4,492,799).

(2) The process (1) in which the reaction is carried out at −15° C. by using sodium iodide (NaI) for higher reactivity (Examples in WO02/08172 and WO01/09079).

(3) A process for synthesizing 5-chloro-2-isopropyl-4-pentenoic acid, which comprises quaternary alkylation of diethyl isopropylmalonate with 1,3-dichloro-1-propene in ethanol as a solvent in the presence of sodium ethoxide (NaOC$_2$H$_5$), hydrolysis of the two ester linkages and monodecarboxylation of the resulting dicarboxylic acid ("Akad. Nauk Armyan, S. S. R. Khim. Nauki", 1960, vol. 13 (4), p. 259-262, (Russia)).

(4) A process for synthesizing various 4-pentenoate derivatives, which comprises quaternary alkylation of a diethyl malonate derivative with a chloropropene derivative in toluene as a solvent in the presence of sodium hydride (NaH) and dealkoxycarbonylation of either ester linkage (U.S. Pat. No. 4,492,799).

For synthesis of optically active (S)-(4E)-5-chloro-2-isopropyl-4-pentenoates and their analogues, the following processes have been reported.

(5) A process for producing ethyl (S)-(4E)-5-chloro-2-isopropyl-4-pentenoate, which comprises adding porcine liver esterase (Roche Diagnostics, Technical Grade) all at once to the racemic ethyl (4E)-5-chloro-2-isopropyl-4-pentenoate obtained by the process (2) (WO01/09079).

(6) A process for producing (S)-(4E)-5-chloro-2-isopropyl-4-pentenoic acid, which comprises hydrolyzing the racemic ethyl (4E)-5-chloro-2-isopropyl-4-pentenoate obtained by the process (2), treating the resulting racemic (4E)-5-chloro-2-isopropyl-4-pentenoic acid with optically active cinchonidine for diastereomeric salt formation, separating the (S)-diastereomer salt by recrystallization and treating the (S)-diastereomeric salt with an acid (WO01/09079).

The reports of the processes (1), (3) and (4), however, are silent about the E/Z ratio of the double bond in the 5-chloro-2-isopropyl-4-pentenoates. Further, while the process (2) was reported to give the E-isomers of a 5-chloro-2-isopropyl-4-pentenoate in yields of 84% and 76%, reproduction of experiments disclosed therein by the present inventors did not gave the E-isomer in the reported yield, but in a yield of only about 4.2%. Thus, it has been difficult to selectively synthesize the E-isomer of 5-chloro-2-isopropyl-4-pentenoates in high yields without isomerization to the Z-form.

Further, because the use of lithium diisopropylamide (LDA) requires that the reaction temperature must be kept thermostatically at such an extremely low temperature as −78° C., and because LDA is prepared from expensive n-butyllithium (n-BuLi), the process (1) is unsuitable for industrial mass production for economical reasons and in view of operational difficulties and gives the product in such a low yield as 46%. The process (2) has a problem that the product is obtained in a low yield and is difficult to purify because methyl isopentanoate as the starting material undergoes side reactions such as self-condensation. The process (3) has a problem that esterification of 5-chloro-2-isopropyl-4-pentenoic acid, which is obtainable in a 23% yield, gives a 5-chloro-2-isopropyl-4-pentenoate in a still lower yield. The process (4) is economically and operationally unsuitable for industrial mass production in view of the use of NaH.

The report of the process (5) does not sufficiently disclose the reaction conditions for production of an optically active isomer and keeps it totally unclear how to obtain the desired compound at all. The processes (5) and (6) are unsuitable for industrial mass production because the use of the process (2) for production of the racemate to be resolved lowers the total yield considerably.

DISCLOSURE OF THE INVENTION

The present invention has been accomplished to solve the above-mentioned problems and provides a process for producing a (4E)-5-chloro-2-isopropyl-4-pentenoate using inexpensive starting material and reagents. The process of the present invention can selectively produce the E-form in a high yield through simple reactions and is suitable for industrial mass production. The present invention also provides a process for producing an (S)-(4E)-5-chloro-2-isopropyl-4-pentenoate in a high yield and in a high enantio excess by optical resolution of the resulting (4E)-5-chloro-2-isopropyl-4-pentenoate.

Namely, the present invention provides the followings.

1. A process for producing a (4E)-5-chloro-2-isopropyl-4-pentenoate represented by the following formula (4) (wherein R is a lower alkyl group or an aralkyl group), which comprises reacting a compound represented by the following formula (2) in the presence of an aprotic solvent (II) with a base (II) and then with (1E)-1,3-dichloro-1-propene to give a compound represented by the following formula (3), and dealkoxycarbonylating either ester in the compound represented by the following formula (3).

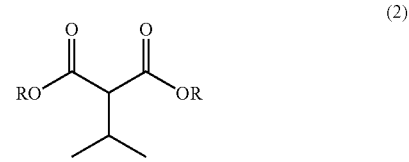

(2)

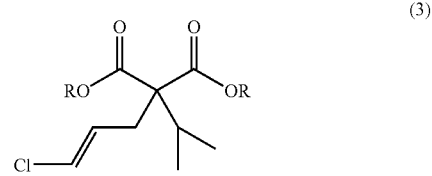

(3)

-continued

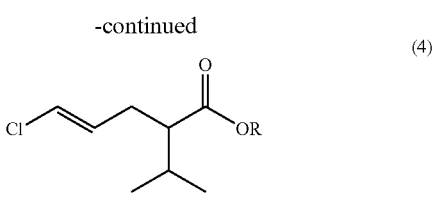

(4)

2. The process according to 1, wherein the base (II) is a metal alkoxide represented by the formula $M^2OR^2$ (wherein $M^2$ is Na or K, and $R^2$ is a lower alkyl group).
3. The process according to 2, wherein the compound represented by the formula (2) is reacted with the metal alkoxide represented by the formula $M^2OR^2$ (wherein $M^2$ and $R^2$ are the same as defined above) as the base (II) in the presence of the aprotic solvent (II), and then an alcohol represented by the formula $R^2OH$ produced as a by-product is removed before the reaction with (1E)-1,3-dichloro-1-propene.
4. The process according to any one of 1 to 3, wherein the aprotic solvent (II) consists of at least one solvent selected from the group consisting of toluene, xylene, benzene, heptane, dimethylformamide, dimethylacetamide, N-methylpyrrolidinone, dimethyl sulfoxide, diethylene glycol dimethyl ether, tetrahydrofuran, t-butyl methyl ether and sulfolane.
5. The process according to any one of 1 to 4, wherein the compound represented by the formula (2) is a compound obtained by reacting a compound represented by the following formula (1) with a base (I) and then with an isopropyl halide in an aprotic solvent (I) (wherein R is the same as defined above).

(1)

6. The process according to 5, wherein the base (I) is a metal alkoxide represented by the formula $M^1OR^1$ (wherein $M^1$ is Na or K, and $R^1$ is a lower alkyl group).
7. The process according to 6, wherein the compound represented by the formula (1) is reacted with the metal alkoxide represented by the formula $M^1OR^1$ (wherein $M^1$ and $R^1$ are the same as defined above) in the presence of the aprotic solvent (I), and then an alcohol represented by the formula $R^1OH$ produced as a by-product is removed before the reaction with the isopropyl halide.
8. The process according to any one of 5 to 7, wherein the compound represented by the formula (1) is reacted with at least 1 molar equivalent of the isopropyl halide, and then the isopropyl halide is removed until the amount of the isopropyl halide reaches 5 mol % or below, based on the resulting compound represented by the formula (2).
9. The process according to any one of 5 to 8, wherein the aprotic solvent (I) consists of at least one solvent selected from the group consisting of toluene, xylene, benzene, heptane, dimethylformamide, dimethylacetamide, N-methylpyrrolidinone, dimethyl sulfoxide, diethylene glycol dimethyl ether, tetrahydrofuran, t-butyl methyl ether and sulfolane.
10. The process according to any one of 1 to 9, wherein the dealkoxycarbonylation is carried out in a polar solvent in the presence of water and an inorganic salt.
11. The process according to any one of 5 to 10, wherein after the compound represented by the formula (2) is obtained, the reaction which gives the compound represented by the formula (3) is carried out in the same vessel.
12. A process for producing an (S)-(4E)-5-chloro-2-isopropyl-4-pentenoate represented by the following formula (5) (wherein R is the same as defined above), which comprises optically resolving a (4E)-5-chloro-2-isopropyl-4-pentenoate represented by the formula (4) obtained by the process as defined in any one of 1 to 11.

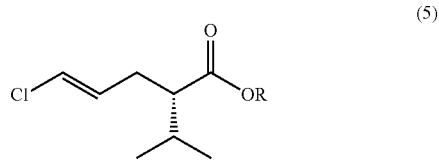

(5)

BEST MODE FOR CARRYING OUT THE INVENTION

Hereinafter, the compound represented by the formula (1) is also referred to as the compound (1). The other compounds are referred to similarly.

The process of the present invention is outlined by the following formula but is not restricted to the following formula.

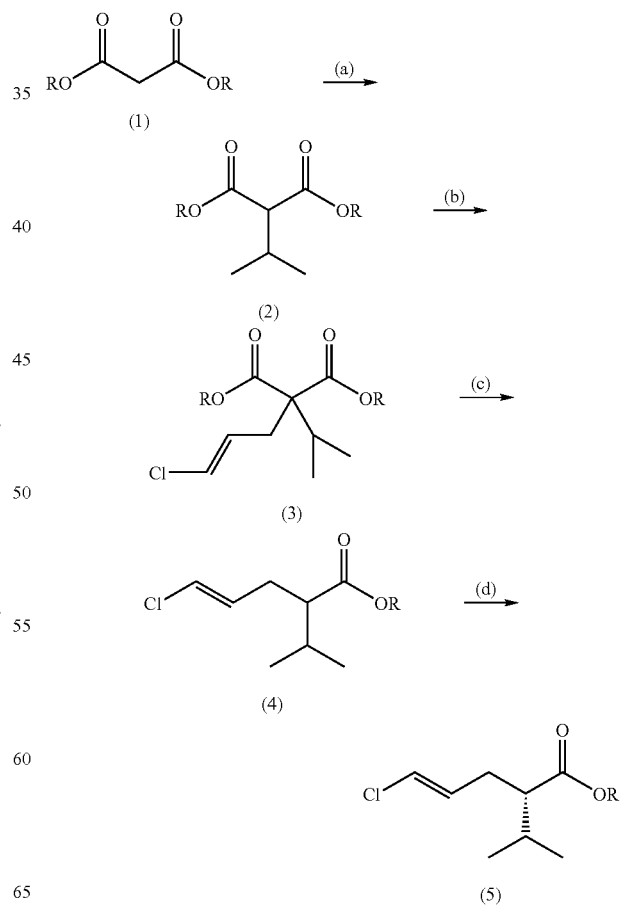

Namely, the compound (1) is subjected to a step (hereinafter referred to as step (a)) of reacting the compound (1) with a base (I) in an aprotic solvent (I) and then with an isopropyl halide to give the compound (2). The compound (2) is subjected to a step (hereinafter referred to as step (b)) of reacting the compound (2) with a base (II) in the presence of an aprotic solvent (II) and then with (1E)-1,3-dichloro-1-propene to give the compound (3). The compound (3) is subjected to a step (hereinafter referred to as step (c)) of dealkoxycalbonylating either ester to give the compound (4). The compound (4) is subjected to a step (hereinafter referred to as step (d)) of optically resolving the compound (4) to give the compound (5) in the (S)-form.

Herein, R is a lower alkyl group or an aralkyl group. The lower alkyl group means a $C_{1-4}$ alkyl group such as a methyl group, an ethyl group, a n-propyl group, an iso-propyl group, a n-butyl group, a sec-butyl group, an iso-butyl group or a tert-butyl group.

The aralkyl group means an aryl-substituted lower alkyl group, preferably a lower alkyl group substituted with one or two aryl groups. The aryl group is a phenyl, 1-naphthyl or 2-naphthyl group which may have one or more substituents on the ring. The substituents are preferably lower alkyl groups. The aralkyl group may, for example, be a benzyl group or a diphenylmethyl group. R is preferably a lower alkyl group, particularly preferably a methyl group.

As the base (I) and the base (II), metal hydrides, metal alkoxides, lithium diisopropylamide (LDA), lithium hexamethyldisilazide, pyridine, triethylamine, inorganic bases and the like may be used. It is particularly preferred to use a metal alkoxide represented by the formula $M^1OR^1$ as the base (I) and a metal alkoxide represented by the formula $M^2OR^2$ as the base (II) (wherein $M^1$ and $M^2$ are Na or K, and $R^1$ and $R^2$ are lower alkyl groups) because they are highly reactive and handleable and economically advantageous.

As the metal alkoxides represented by the formulae $M^1OR^1$ and $M^2OR^2$, sodium methoxide ($NaOCH_3$), sodium ethoxide ($NaOC_2H_5$), sodium tert-butoxide (t-BuONa) and potassium tert-butoxide (t-BuOK) may be mentioned, respectively. Inexpensively available $NaOCH_3$ and $NaOC_2H_5$, especially in the form of powder or solution, are preferred. When these metal alkoxides are in the form of solutions, it is preferred that the metal alkoxide represented by the formula $M^1OR^1$ is in the form of a solution in an alcohol represented by the formula $R^1OH$, and the metal alkoxide represented by the formula $M^2OR^2$ is in the form of a solution in an alcohol represented by the formula $R^2OH$ (wherein $M^1$, $M^2$, $R^1$ and $R^2$ are the same as defined above). The concentrations of the solutions are preferably from 5 to 35 mass %, particularly preferably from 15 to 35 mass %. These metal alkoxides may be prepared from an alkali metal and a lower alcohol before use. These metal alkoxides are advantageously used because they are more handleable and inexpensive than conventionally used bases such as LDA and NaH.

The aprotic solvent (I) and the aprotic solvent (II) are preferably aromatic hydrocarbon solvents such as toluene, xylene and benzene; aliphatic hydrocarbon solvents such as hexane and heptane; amide solvents such as dimethylformaide (DMF), dimethylacetamide (DMA) and N-methylpyrrolidinone (NMP); sulfoxide solvents such as dimethyl sulfoxide (DMSO); sulfone solvents such as sulfolane; or ether solvents such as diethylene glycol dimethyl ether (DME), diglyme, tetrahydrofuran (THF) and t-butyl methyl ether (TBME). These solvents may be used singly or in the form of a solvent mixture of two or more. In the present invention, the aprotic solvent (I) and the aprotic solvent (II) are preferably a solvent mixture of toluene with an amide solvent or sulfolane in view of prevention of impurity formation, handleability and recovery and reuse of the solvent. The (amide solvent or sulfolane) and toluene are mixed preferably in an (amide solvent or sulfolane)/toluene ratio (volume ratio) of from 1/2 to 1/50, in particular from 1/3 to 1/10.

Now, the steps (a) to (d) will be described sequentially. In the step (a), as the compound (1), dimethyl malonate, diethyl malonate, diisopropyl malonate or the like, preferably dimethyl malonate, is used. As the isopropyl halide, isopropyl bromide, isopropyl chloride, isopropyl iodide or the like is used. Malonic diesters, isopropyl halides and (1E)-1,3-dichloro-1-propene are well-known compounds available industrially at low prices. It is usually preferred to obtain these compounds as commercial products. Such commercial products can usually be used without purification, though they may be purified, if necessary.

The step (a) involves tertiary alkylation which gives the compound (2) by reacting the compound (1) in an aprotic solvent (I) with a base (I) and then with an isopropyl halide.

In the step (a), the amount of the isopropyl halide is preferably at least 1.0 molar equivalent based on the compound (1) in view of the conversion during the reaction, more preferably from 1.0 to 50.0 molar equivalents, particularly preferably from 1.0 to 3.0 molar equivalents in view of handleability, volume efficiency and cost. The isopropyl halide is preferably isopropyl bromide in view of reactivity and price.

The amount of the base (I) is preferably 0.9 to 5 molar equivalents, in particular from 1.0 to 3.0 molar equivalents, based on the compound (1). The amount of the aprotic solvent (I) is preferably from 0.5 to 20 ml per 1 g of the compound (1).

In the step (a), a metal iodide such as sodium iodide (NaI) and potassium iodide (KI) or a metal bromide such as sodium bromide (NaBr) and potassium bromide (KBr) may be added to further increase reactivity. The amount of such a metal iodide or bromide, if added, is preferably from 1 mol % to 100 mol %, in particular from 1 mol % to 10 mol %, based on the isopropyl halide.

In the step (a), the reaction temperature is preferably from +30 to +180° C., in particular from +70° C. to +140° C., and the reaction time is preferably from 1 to 30 hours. The reaction pressure is preferably atmospheric pressure or above, in particular atmospheric pressure.

In the step (a), the reaction is preferably carried out by a method (a-1) in which the compound (1), the base (I) and the isopropyl halide are added in this order or by a method (a-2) in which the base (I), the compound (1) and the isopropyl halide are added in this order.

In the step (a), as the base (I), a base represented by the previously mentioned formula $M^1OR^1$ ($M^1$ and $R^1$ are the same as defined previously) is preferably used. When a base represented by the formula $M^1OR^1$ is used, it is also preferred to react the compound (1) with the base in the presence of the aprotic solvent (I) first and then with the isopropyl halide in accordance with the method (a-1) or (a-2). The reaction with a base represented by the formula $M^1OR^1$ produces an alcohol represented by the formula $R^1OH$ as a by-product. For example, when the base is $NaOCH_3$, methanol is produced as a by-product, and when the base is $NaOC_2H_5$, ethanol is produced as a by-product. The alcohol produced as a by-product is preferably removed from the reaction system before the reaction with the isopropyl halide. The alcohol is preferably removed by evaporation, usually by heating before the addition of the isopropyl halide. It is preferred to remove a protic solvent such as the alcohol produced as a by-product in view of conversion and reaction time, though it does not halt the progress of the reaction even if it remains in the reaction system.

In the step (a), it is preferred to use the isopropyl halide in an amount of at least 1 molar equivalent based on the compound (1), and remove the remaining isopropyl halide from the reaction system after the reaction. If the isopropyl halide remains in a large amount, the isopropyl halide undergoes a side reaction such as quaternary alkylation of the compound (2) or a reaction with a base represented by the formula $M^2OR^2$ (wherein $M^2$ and $R^2$ are the same as defined previously) such as $NaOCH_3$ in the subsequent step (b) to unfavorably lower the yield of the compound (3) as the desired product. It is preferred to remove the isopropyl halide until the amount of the isopropyl halide reaches 5 mol % or below, particularly 1 mol % or below, based on the compound (2). The removed isopropyl halide may be reused for the reaction in the step (a).

The step (b) involves quaternary alkylation which gives the compound (3) by reacting the compound (2) with a base (II) in the presence of an aprotic solvent (II) and then with (1E)-1,3-dichloro-1-propene.

In the step (b), the amount of (1E)-1,3-dichloro-1-propene is preferably from 0.9 to 50.0 molar equivalents based on the compound (2), particularly preferably from 1.0 to 3.0 molar equivalents in view of handleability, volume efficiency and cost. The excess of (1E)-1,3-dichloro-1-propene, if any, may be recovered for reuse in the step (b).

The amount of the base (II) is preferably 0.9 to 5 molar equivalents, in particular from 0.9 to 3.0 molar equivalents, based on the compound (2). An excess of the base (II) may cause a side reaction of the unreacted base (II) with (1E)-1,3-dichloro-1-propene.

The aprotic solvent (II) is used preferably in an amount of from 0.5 to 20 ml per 1 g of the compound (2).

In the step (b), a metal iodide such as NaI and KI or a metal bromide such as NaBr and KBr may be added to further increase reactivity. The amount of such a metal iodide or bromide, if added, is preferably from 1 mol % to 100 mol %, in particular from 1 mol % to 10 mol %, based on (1E)-1,3-dichloro-1-propene.

In the step (b), the reaction temperature is preferably from +30 to +180° C., in particular from +70° C. to +140° C., and the reaction time is preferably from 1 to 30 hours. The reaction pressure is preferably atmospheric pressure or above, in particular atmospheric pressure.

In the step (b), the reaction is preferably carried out by a method (b-1) in which the compound (2), the base (II) and (1E)-1,3-dichloro-1-propene are added in this order or a method (b-2) in which the base (II), the compound (2) and (1E)-1,3-dichloro-1-propene are added in this order.

In the step (b), as the base (II), a base represented by the previously mentioned formula $M^2OR^2$ ($M^2$ and $R^2$ are the same as defined previously) is preferably used. When a base represented by the formula $M^2OR^2$ is used, it is also preferred to react the compound (2) with the base in the presence of the aprotic solvent (II) first and then with (1E)-1,3-dichloro-1-propene in accordance with the method (b-1) or (b-2). The reaction with a base represented by the formula $M^2OR^2$ produces an alcohol represented by the formula $R^2OH$ as a by-product. For example, when the base is $NaOCH_3$, methanol is produced as a by-product, and when the base is $NaOC_2H_5$, ethanol is produced as a by-product. The alcohol produced as a by product is preferably removed from the reaction system before the reaction with (1E)-1,3-dichloro-1-propene. The alcohol is preferably removed by evaporation, usually by heating before the addition of (1E)-1,3-dichloro-1-propene. It is preferred to remove a protic solvent such as the alcohol produced as a by-product in view of conversion and reaction time, though it does not halt the progress of the reaction even if it remains in the reaction system.

In the process of the present invention, when the step (a) is immediately followed by the step (b), it is preferred to carry out the reactions successively in the same reaction vessel without purification of the compound (2) produced in the step (a). Namely, production of the compound (2) in the step (a) is preferably followed by the reaction in the step (b) in the same reaction vessel to give the compound (3).

It is advantageous to carry out the step (a) and the step (b) successively in the same vessel for industrial production because it shortens the reaction time and facilitates the operations. However, if the step (a) and the step (b) are carried out successively, the residual isopropyl halide remaining after the reaction in the step (a) reacts with the diisopropyl malonate (the formula 2) to lower the yield in the step (b). Therefore, it is preferred to remove the isopropyl halide from the reaction system after completion of the step (a) in order to prevent decrease in the yield.

In the present invention, the step (b) is followed by the step (c).

The step (c) involves dealkoxycarbonylation which gives a (4E)-5-chloro-2-isopropyl-4-pentenoate represented by the formula (4) by dealkoxycarbonylating either ester in the compound (3). Herein, "dealkoxycarbonylation" means a reaction which replaces an ester moiety (—COOR moiety) by a hydrogen atom.

In the process of the present invention, the dealkoxycarbonylation is preferably carried out in a polar solvent in the presence of water and an inorganic salt under heating.

The inorganic salt to be used in the step (c) is preferably an alkali metal halide, such as sodium chloride (NaCl), lithium chloride (LiCl) or sodium bromide (NaBr), particularly preferably NaCl or LiCl.

In the step (c), the amount of the inorganic salt is preferably from 0.5 to 50 molar equivalents, in particular from 0.5 to 10 molar equivalents, based on the compound (3). In the step (c), water is used in an amount of from 0.1 to 50 molar equivalents, in particular from 0.1 to 3 molar equivalents, based on the compound (3).

The polar solvent may be an amide solvent such as DMF, DMA or NMP, a sulfoxide solvent such as DMSO, a sulfone solvent such as sulfolane or an ether solvent such as DME or THF. As the polar solvent, a single polar solvent or a solvent mixture of two or more polar solvents may be used. As the polar solvent, sulfolane is preferred because it secures high reactivity, does not decompose during the reaction and has an operationally appropriate boiling point. The amount of the polar solvent is preferably from 2 to 30 times, in particular from 5 to 15 times, by mass, that of the compound (3).

In the process of the present invention, the compound (2) produced in the step (a), the compound (3) produced in the step (b) and the compound (4) produced in the step (c) are preferably subjected to post-treatment and/or purification treatment, respectively, to meet the purpose, for example, by adding water or aqueous sodium chloride and then a water-immiscible organic solvent such as dichloromethane, toluene, ethyl acetate, butyl acetate, t-butyl methyl ether, diisopropyl ether or diethyl ether to the crude reaction solution and separating then concentrating and distilling the organic layer to isolate the desired compound (treatment 1), by washing the organic layer obtained in the treatment 1 with water and/or aqueous sodium chloride and then concentrating and distilling the organic layer to isolate the desired compound (treatment 2), or by cooling the crude reaction solution and distilling it under reduced pressure (treatment 3). Further, if necessary, the treatments 1 to 3 may be preceded or followed by filtration or addition of an adsorbent such as activated carbon. It is especially preferred to add an adsorbent to the product of the step (c) for successful removal of tarry substances from the reaction product.

The (4E)-5-chloro-2-isopropyl-4-pentenoate (formula 4) obtained by the process of the present invention is a compound known to be useful as an intermediate for an agrochemical or a medicine. The compound (4) is especially useful as an intermediate for an insecticide or an antihypertensive agent (WO01/9079). The compound (4) is usually obtained as a racemate by the process and, if necessary, may be subjected to optical resolution (step (d)). The step (d) involves optical resolution of the (4E)-5-chloro-2-isopropyl-4-pentenoate represented by the formula (4) which gives an optically active (S)-(4E)-5-chloro-2-isopropyl-4-pentenoate (formula 5).

The optical resolution may be carried out, for example, by the following methods.

Method (d-1): a method comprising hydrolyzing the racemic compound (4) into the corresponding racemic carboxylic acid, treating the carboxylic acid with an optically active base to give diastereomeric salts, separate the desired diastereomeric salt by recrystallization, treating the separated diastereomeric salt with an acid to liberate a carboxylic acid, and esterifying the carboxylic acid.

Method (d-2): a method comprising passing the compound (4) through an optical isomer separation column to obtain the desired optically active isomer.

Method (d-3): a method comprising treating the compound (4) with lipase or esterase to selectively hydrolyze either optically active isomer to the desired optically active ester.

In the method (d-1), as the optically active base, cinchonidine, phenethylamine or the like may be used.

In the method (d-2), preparatory high performance liquid chromatography using an optical isomer separation column, especially using a SMB system (Simulated Moving Bed system), is preferred.

In the method (d-3), the lipase or esterase (hereinafter referred to collectively as "enzyme") may be an enzyme for reagent, medical or industrial use. When an enzyme which acts on the (R)-form of the compound (4) is used in the method (d-3), the enzyme catalyzes the hydrolysis of the (R)-form of the compound (4) into the optically active compound (6) but does not catalyze the hydrolysis of the compound (5) as the (S)-isomer of the compound (4). Consequently, after the enzymatic reaction, the reaction solution contains the optically active compound (5) and the optically active compound (6). The compound (5) and the compound (6) can be separated by a separation technique utilizing the difference in properties between the —COOR group in the compound (5) and the —COOH group in the compound (6), and the desired compound (5) is recovered. Thus, optical resolution is attained.

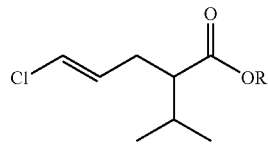

(4)

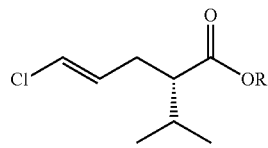

(5)

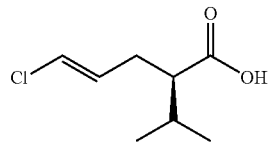

(6)

The step (d) is preferably carried out by the method (d-3) because it gives the desired compound (5) in a high yield and in a high ee without special equipment, with easy operations and is suitable for industrial mass production. Now, as a preferred embodiment of optical resolution, the method (d-3) is described in reference to an enzyme which acts on the (R)-form.

The enzyme to be used in the method (d-3) may be of any origin without particularly restrictions and may be, for example, of yeast (*Candida Antarctica*) origin in the case of lipase or of porcine liver origin in the case of esterase. For example, as a porcine liver esterase, the enzyme used for optical resolution by Johnston DBR et al. as disclosed in J. Am. Chem. Soc., vol. 100, pp. 313-315 (1978) may be used. A protein expressed by introduction of the gene of an enzyme isolated from such a lipase or esterase into a vector may be used as the enzyme in the method (d-3).

The lipase or esterase may be immobilized to an inert support in view of facilitation of the operation. The inert support is preferably celite, porous glass beads, cellulose or its derivative, chitin or its derivative, calcium alginate, κ-carrageenan, polystyrene or its derivative, polyurethane, polyacrylamide, nylon, polyvinyl alcohol, a polyethylene glycol derivative, a polypropylene glycol derivative or a polybutadiene derivative, particularly preferably porous glass beads, chitin or its derivative or calcium alginate.

The amount of the lipase or esterase depends on its hydrolytic activity on the compound (4) as the starting material of the optical resolution and is usually from $1 \times 10^{-5}$ to $1 \times 10$ mass %, preferably from $1 \times 10^{-5}$ to 5 mass %, based on the total amount of the compound (4).

Optical resolution by the method (d-3) may, if necessary, use a solvent and preferably uses a solvent to facilitate the operation. The solvent to be used may be an aqueous solvent, an organic solvent or a solvent mixture thereof, preferably an aqueous solvent because the compound (5) is obtained in high yield and in high ee. The solvent may be a single solvent or a mixture of two or more solvents, preferably of an aqueous solvent and an organic solvent.

The amount of the solvent is from 0.1 to 50 mass %, in particular from 1 to 30 mass %, based on the compound (4).

The aqueous solvent may be water or a buffer selected from commonly used buffers such as phosphate buffer, citrate buffer, HEPES buffer, TRIS buffer, acetate buffer and MES buffer.

The organic solvent is selected from ordinary organic solvents such as alcohol solvents such as methanol, ethanol, propanol, isopropanol, butanol, isobutanol and t-butyl alcohol; aliphatic hydrocarbon solvents such as pentane, hexane and heptane; aromatic hydrocarbon solvents such as benzene, toluene and xylene; halogenated hydrocarbon solvents such as methylene chloride, chloroform and carbon tetrachloride; ether solvents such as diethyl ether, diisopropyl ether, t-butyl methyl ether, tetrahydrofuran and dioxane; ketone solvents such as acetone, methyl ethyl ketone and methyl isobutyl ketone; and other solvents such as acetonitrile, N,N-dimethylformamide and dimethyl sulfoxide. Because of the possible catalytic action of the enzyme on ester solvents, it is preferred to select, if used, an ester solvent which resists the catalytic action of the enzyme. Further, because transesterification may occur between ester solvents and the starting material, it is preferred to select an ester solvent which does not undergo transesterification. These organic solvents may be used singly or as a mixture of two or more.

Optical resolution by the method (d-3) is preferably performed by adding the compound (4) to a solution of the enzyme in the solvent. The compound (4) may be added all at once or gradually, preferably gradually in the process of the present invention. As described above, in the method (d-3), the compound (6), which is an optically active carboxylic acid, is produced. Because the carboxylic acid has a strong denaturing effect on the enzyme, the enzymatic activity tends to decrease as the enzyme is exposed longer to the carboxylic acid with a progressively increasing concentration of the carboxylic acid. Therefore, the enzymatic treatment of the compound (4) is preferably performed by gradually adding the compound (4) to the reaction system, because it is possible to prevent sudden increase in the concentration of the compound (6) in the reaction system and denaturation and loss of activity of the enzyme.

"Gradual addition" is conceptually opposed to "batch addition" which means that the compound (4) is added all at once, and means that the compound (4) is added at least once after initiation of the reaction of the compound (4). Gradual addition is preferably performed by introducing an arbitrary amount of the compound (4) to the reaction system at least twice after initiation of the reaction or by continuously introducing the compound (4) over a certain period of time after initiation of the reaction by addition of the enzyme. Such an operation may be carried out once or at least twice during the reaction.

The compound (4) may be added, for example, by adding the compound (4) directly or after dissolved in a solvent, to a solution of the enzyme in a solvent, preferably with stirring.

For addition of the compound (4) or its solution, pneumatic pressure, a pump or gravity feed may be used without any particular restrictions.

The feed rate of the compound (4) is preferably from 0.005 to 0.1 mol/hour, particularly preferably from 0.01 to 0.05 mol/hour, per 1 mg of the enzyme, though it is not particularly restricted. The feed rate may be constant or varied. The compound (4) is added over preferably from 4 to 30 hours, particularly preferably from 5 to 20 hours, though the duration of addition is not particularly restricted as long as it is within an industrially acceptable range.

It is preferred to add the compound (4) in a total amount of from 0.1 to 60 mass %, particularly from 1 to 50 mass %, in view of production on an industrial scale, in terms of the total concentration of the compound (4) (based on the sum of the amount of the solvent and the total amount of the compound (4)).

The enzymatic reaction in the step (d) usually requires control of the reaction conditions such as reaction temperature and the pH of the reaction solution. The reaction conditions are appropriately chosen by considering the enzymatic reaction, racemization of the reaction product and formation of by-products. When a solvent is used, the reaction temperature is usually preferred to be from −20 to +90° C., particularly from 0 to +60° C., particularly preferably from +25 to 45° C. in view of reaction rate. The pH of the reaction solution is preferably from 1 to 10, particularly from 3 to 9, particularly preferably from 7.5 to 8.5 in view of reaction rate and the purity of the resulting compound (5). The compound (6) produced in the reaction system with the progress of the optical resolution can shift the pH of the reaction solution outside the preferable range. In such a case, it is preferred to adjust the pH of the reaction solution by adding an inorganic base like an aqueous solution of an alkali metal hydroxide such as sodium hydroxide or potassium hydroxide or an alkali metal carbonate such as sodium carbonate or potassium carbonate or aqueous ammonia to the reaction solution.

The reaction time is not particularly restricted as long as the enzyme retains its activity, and the reaction proceeds. However, in general, the reaction time after completion of the gradual addition is preferably from 1 hour to 10 days, particularly preferably from 1 to 96 hours, in view of industrial production.

The compound (5) obtained in the step (d) is preferably subjected to post-treatment and/or purification treatment, depending on the purpose.

For example, extraction of the crude reaction solution obtained by the above-mentioned reaction by addition of a non-aqueous organic solvent (such as hexane, ethyl acetate, t-butyl methyl ether, methylene chloride, chloroform or diethyl ether) followed by vigorous mixing, subsequent liquid-liquid separation and recovery of the non-aqueous organic solvent may be mentioned. The extraction with a non-aqueous organic solvent may be repeated more than once. The above-mentioned extraction procedure gives the non-aqueous organic solvent containing the compound (5) as the extract and leaves the compound (6) (or the compounds (6) and (7), if the pH is adjusted as described above) (wherein M is an alkali metal atom or $NH_4$) in the aqueous solvent layer.

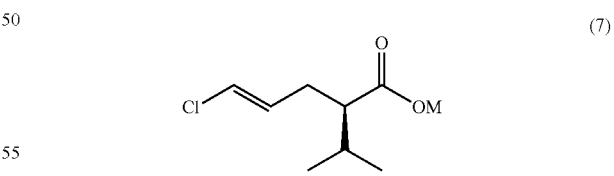

(7)

The non-aqueous organic solvent layer is preferably washed with an aqueous alkali metal carbonate (preferably 5% sodium carbonate solution) to remove the compound (6) from the non-aqueous organic solvent layer. Then, the non-aqueous organic solvent layer is concentrated under reduced pressure or distilled to isolate the compound (5). The isolated compound (5) may be further purified by distillation or the like, if necessary.

The aqueous solvent layer obtained after the extraction contains the compound (6) and/or the compound (7). The compound (6) can be recovered from the aqueous solvent layer containing the compound (6) and/or the compound (7), by acidifying the aqueous solvent layer with hydrochloric acid or the like (preferably to pH 4 or below), extracting it with a non-aqueous organic solvent (such as hexane, ethyl acetate, t-butyl methyl ether, methylene chloride, chloroform or diethyl ether) and then separating and concentrating the non-aqueous organic solvent layer. The recovered compound (6) may be esterified with an alcohol compound represented by the formula ROH in the presence of sulfuric acid and racemized for reuse in the step (d) (wherein R is the same as defined above).

A preferred embodiment of the process of the present invention is the following process for producing the compound (5a). Namely, the compound (1a) is isopropylated to the compound (2a), then the compound (2a) is reacted with (1E)-1,3-dichloro-1-propene to give the compound (3a), and either ester in the compound (3a) is dealkoxycarbonylated to give the compound (4a) in a high yield without isomerization. Optical resolution of the compound (4a) affords the compound (5a) in a high yield and in a high ee.

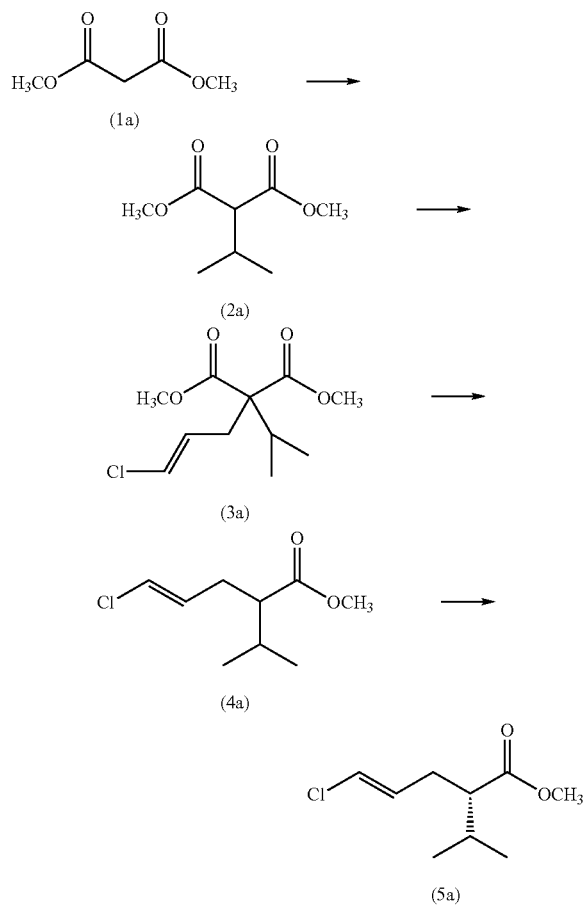

EXAMPLES

Now, the present invention will be described specifically in reference to Examples. However, the present invention is by no means restricted to these specific Examples. Hereinafter, gas chromatography will be referred to as GC, and the amount of an enzyme is given in "Units". 1 Unit is defined as the activity of an enzyme required to convert 1 μmol of ethyl butyrate to 1 μmol of butyric acid per 1 minute at 25° C. The structures of the formed compounds were identified by referring to previously available data. The enantiomeric purity and the enantiomeric excess were determined by GC using Lipodex E 50 m×0.25 mm (Macherey-Nagel) as the column.

Example 1

Example (1) of Synthesis of methyl (4E)-5-chloro-2-isopropyl-4-pentenoate

Step (a):

A 5 L flask equipped with a stirrer, a thermometer, a condenser and a distilling apparatus was loaded with 28% NaOCH$_3$ in methanol (373.8 g), toluene (1250 ml), dimethylformamide (375 ml), and dimethyl malonate (250 g) in toluene (375 ml) was added thereto dropwise. The resulting mixture was gradually heated while the methanol formed as a by-product and the methanol originating from the 28% NaOCH$_3$ in methanol were removed. The distillate obtained under heating was analyzed by GC, and the heating was stopped when the methanol content of the distillate reached 1% or below. After the system was cooled to 80-90° C., isopropyl bromide (264.8 g) in toluene (375 ml) was added, and then, the system was heated with stirring for 20 hours. After confirmation of almost complete disappearance of the starting materials by GC, methanol (200 ml) was added, and the system was heated gradually to remove the remaining isopropyl bromide. The reaction system was cooled to 80° C., 28% NaOCH$_3$ in methanol (318.4 g) was added dropwise. After addition of toluene (600 ml), the reaction system was gradually heated as previously described to remove methanol, while the distillate obtained under heating was analyzed by GC, and the heating was stopped when the methanol content of the distillate reached 0.5% or below.

Step (b):

After the step (a), the reaction system was cooled to 90° C., and (1E)-1,3-dichloro-1-propene (192.3 g) in toluene (250 ml) was added. After 2 hours of heating with stirring, the system was cooled to 50° C., and water was added to terminate the reaction. The aqueous layer was extracted with diisopropyl ether (IPE), and the extract was combined with the organic layer and washed with water and 5% aqueous NaCl, successively. The solvent was evaporated under reduced pressure to give dimethyl 2-[(2E)-3-chloro-2-propenyl]-2-isopropylmalonate (409.7 g). The product contained 87% (GC purity) of dimethyl 2-[(2E)-3-chloro-2-propenyl]-2-isopropylmalonate and at most 0.5% (measured by GC) of isopropyl bromide, but did not contain the Z-isomer.

$^1$H NMR (400 MHz, CDCl$_3$): 0.98 (d, 6H, J=6.76), 2.31 (m, 1H), 2.62 (dd, 2H, J=1.16, 7.64), 3.73 (s, 6H), 5.89 (dt, 1H, J=7.60, 13.19), 6.01 (dt, 1H, J=1.16, 13.19).

$^{13}$C NMR (400 MHz, CDCl$_3$): 18.33, 32.41, 35.14, 51.94, 62.06, 119.83, 128.87, 170.66.

Step (c):

Dimethyl 2-[(2E)-3-chloro-2-propenyl]-2-isopropylmalonate (408.0 g) obtained in the step (b) was heated with DMSO (2774 g), H$_2$O (59 g) and NaCl (96 g) to 180° C. and then stirred for 7 hours until almost perfect completion of the reaction was confirmed by GC. After the reaction system was cooled, the solid was filtered off, and the filter cake was washed with IPE. After addition of water, the organic layer was extracted with IPE, and the resulting organic layer was washed with water and 5% aqueous NaCl. The organic layer was evaporated under reduced pressure and distilled under reduced pressure to give methyl (4E)-5-chloro-2-isopropyl-4-pentenoate (254.2 g) in a 75% yield, based on dimethyl malonate as the starting material. The product of the step (c) did not contain the Z-isomer.

$^1$H NMR (400 MHz, CDCl$_3$): 0.91 (d, 1H, J=6.96), 0.95 (d, 1H, J=6.60), 1.88 (m, 1H) 2.19-2.38 (m, 3H), 3.67 (s, 3H), 5.82 (dt, 1H, J=7.26, 13.19), 5.99 (dd, 1H, J=5.99, 13.19).

$^{13}$C NMR (400 MHz, CDCl$_3$): 19.95, 20.03, 30.14, 30.75, 118.60, 130.88, 174.74.

Example 2

Example (2) of Synthesis of methyl (4E)-5-chloro-2-isopropyl-4-pentenoate

Step (c):

Dimethyl 2-[(2E)-3-chloro-2-propenyl]-2-isopropylmalonate (10 g) obtained in the step (b) in Example 1 was heated with sulfolane (102 ml), H$_2$O (1 g) and NaCl (3.5 g) to 225° C. and then stirred for 13 hours until completion of the reaction was confirmed by GC. The reaction system was cooled and evaporated under reduced pressure to give crude methyl (4E)-5-chloro-2-isopropyl-4-pentenoate (12.1 g). The crude product afforded methyl (4E)-5-chloro-2-isopropyl-4-pentenoate (10 g) after dilution with IPE and removal of the residual sulfolane by washing with water. NMR analysis of the product agreed with the data obtained in Example 1. The product of the step (c) did not contain the Z-isomer.

Example 3

Example (1) of Enzymatic Optical Resolution of methyl (4E)-5-chloro-2-isopropyl-4-pentenoate To a solution of 614 Units of porcine liver esterase (Roche Diagnostics, Technical Grade) in phosphate buffer (pH 7.0, 5 mmol/l, 230 mL) maintained at 35-40° C., racemic methyl (4E)-5-chloro-2-isopropyl-4-pentenoate (20 g) obtained in the same manner as in Example 2 was fed at a rate of 0.065 g/min with a tubing pump, while the reaction system was stirred with a stirring blade to disperse the starting material throughout the reaction system. After the starting material was fed continuously over 5 hours and 10 minutes, the reaction was continued for 21 hours under the same conditions. The starting material was fed to a total concentration of 8 mass %.

The reaction product was extracted with t-butyl methyl ether, and the organic layer was washed with 5% aqueous sodium carbonate to transfer (R)-(4E)-5-chloro-2-isopropyl-4-pentenoic acid into the aqueous phase. It was found by GC analysis that methyl (S)-(4E)-5-chloro-2-isopropyl-4-pentenoate was obtained in the organic layer in a 96% yield and had an enantiomeric purity of at least 98% ee.

Example 4

Example (2) of Enzymatic Optical Resolution of methyl (4E)-5-chloro-2-isopropyl-4-pentenoate The reaction and the post-treatment in Example 3 were carried out except that racemic methyl (4E)-5-chloro-2-isopropyl-4-pentenoate (20 g) was fed at a rate of 0.017 g/min over 19 hours and 40 minutes, and then the reaction was continued for 6 hours. It was found by GC analysis that methyl (S)-(4E)-5-chloro-2-isopropyl-4-pentenoate was obtained in the organic phase in a 96% yield and had an enantiomeric purity of at least 98% ee.

Example 5

Example (3) of Enzymatic Optical Resolution of methyl (4E)-5-chloro-2-isopropyl-4-pentenoate Optical resolution was carried out in the same manner as in Example 3 except that the pH of the reaction solution was adjusted to 8.0 with 0.5 mol/l aqueous NaOH prior to the feeding of racemic methyl (4E)-5-chloro-2-isopropyl-4-pentenoate (20 g) and kept at 8.0 by means of a pH controller until completion of the reaction. After completion of the reaction, the reaction solution was post-treated in the same manner as in Example 3. It was found by GC analysis that methyl (S)-(4E)-5-chloro-2-isopropyl-4-pentenoate was obtained in the organic phase in a 96% yield and had an enantiomeric purity of at least 98% ee.

Example 6

Example (4) of Enzymatic Optical Resolution of methyl (4E)-5-chloro-2-isopropyl-4-pentenoate The reaction and the post-treatment in Example 3 were carried out except that racemic methyl (4E)-5-chloro-2-isopropyl-4-pentenoate (20 g) was added all at once at the same time as the initiation of the reaction, and the reaction was continued for 26 hours. Methyl (S)-(4E)-5-chloro-2-isopropyl-4-pentenoate was obtained in the organic phase and had an enantiomeric purity of at most 90% ee.

INDUSTRIAL APPLICABILITY

The present invention provides a short process for selectively producing a (4E)-5-chloro-2-isopropyl-4-pentenoate useful as an intermediate for an agrochemical or a medicine in a high yield without isomerization and a process for producing a (S)-(4E)-5-chloro-2-isopropyl-4-pentenoate more useful as an intermediate for an agrochemical or a medicine in a high yield and in a high ee by optical resolution of the (4E)-5-chloro-2-isopropyl-4-pentenoate obtained by the above-mentioned process. The processes of the present invention use more inexpensive and handleable reagents than conventional processes and therefore are economically excellent. Further, the processes of the present invention are practical for industrial production because they can attain high yields without special reaction equipment.

The entire disclosures of Japanese Patent Application No. 2002-356651 filed on Dec. 9, 2002 and Japanese Patent Application No. 2003-143256 filed on May 21, 2003 including specifications, claims and summaries are incorporated herein by reference in their entireties.

What is claimed is:

1. A process for producing a (4E)-5-chloro-2-isopropyl-4-pentenoate represented by the following formula (4) (wherein R is a lower alkyl group or an aralkyl group), which comprises reacting a compound represented by the following formula (2) in the presence of an aprotic solvent (II) with a base (II) and then with (1E)-1,3-dichloro-1-propene to give a compound represented by the following formula (3), and dealkoxycarbonylating either ester in the compound represented by the following formula (3)

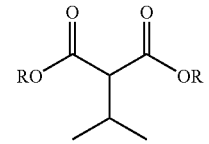
(2)

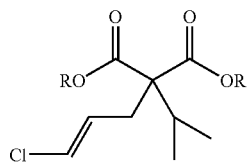
(3)

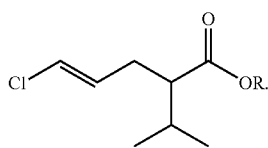
(4)

2. The process according to claim 1, wherein the base (II) is a metal alkoxide represented by the formula $M^2OR^2$ (wherein $M^2$ is Na or K, and $R^2$ is a lower alkyl group).

3. The process according to claim 2, wherein the compound represented by the formula (2) is reacted with the metal alkoxide represented by the formula $M^2OR^2$ (wherein $M^2$ and $R^2$ are the same as defined above) as the base (II) in the presence of the aprotic solvent (II), and then an alcohol represented by the formula $R^2OH$ produced as a by-product is removed before the reaction with (1E)-1,3-dichloro-1-propene.

4. The process according to claim 1, wherein the aprotic solvent (II) consists of at least one solvent selected from the group consisting of toluene, xylene, benzene, heptane, dimethylformamide, dimethylacetamide, N-methylpyrrolidinone, dimethyl sulfoxide, diethylene glycol dimethyl ether, tetrahydrofuran, t-butyl methyl ether and sulfolane.

5. The process according to claim 1, wherein the compound represented by the formula (2) is a compound obtained by reacting a compound represented by the following formula (1) with a base (I) and then with an isopropyl halide in an aprotic solvent (I) (wherein R is the same as defined above)

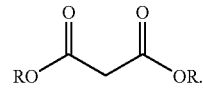
(1)

6. The process according to claim 5, wherein the base (I) is a metal alkoxide represented by the formula $M^1OR^1$ (wherein $M^1$ is Na or K, and $R^1$ is a lower alkyl group).

7. The process according to claim 6, wherein the compound represented by the formula (1) is reacted with the metal alkoxide represented by the formula $M^1OR^1$ (wherein $M^1$ and $R^1$ are the same as defined above) in the presence of the aprotic solvent (I), and then an alcohol represented by the formula $R^1OH$ produced as a by-product is removed before the reaction with the isopropyl halide.

8. The process according to claim 5, wherein the compound represented by the formula (1) is reacted with at least 1 molar equivalent of the isopropyl halide, and then the isopropyl halide is removed until the amount of the isopropyl halide reaches 5 mol % or below, based on the resulting compound represented by the formula (2).

9. The process according to claim 5, wherein the aprotic solvent (I) consists of at least one solvent selected from the group consisting of toluene, xylene, benzene, heptane, dimethylformamide, dimethylacetamide, N-methylpyrrolidinone, dimethyl sulfoxide, diethylene glycol dimethyl ether, tetrahydrofuran, t-butyl methyl ether and sulfolane.

10. The process according to claim 5, wherein the dealkoxycarbonylation is carried out in a polar solvent in the presence of water and an inorganic salt.

11. The process according to claim 5, wherein after the compound represented by the formula (2) is obtained, the reaction which gives the compound represented by the formula (3) is carried out in the same vessel.

12. A process for producing an (S)-(4E)-5-chloro-2-isopropyl-4-pentenoate represented by the following formula (5) (wherein R is the same as defined above), which comprises optically resolving a (4E)-5-chloro-2-isopropyl-4-pentenoate represented by the formula (4) obtained by the process as defined in claim 1

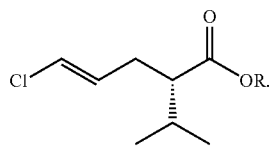
(5)

* * * * *